United States Patent
Leonard

(10) Patent No.: US 8,556,844 B2
(45) Date of Patent: Oct. 15, 2013

(54) SYSTEMS, METHODS, AND DEVICES FOR BLOOD TREATMENT

(75) Inventor: Edward F. Leonard, Bronxville, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 108 days.

(21) Appl. No.: 12/747,785

(22) PCT Filed: Dec. 12, 2008

(86) PCT No.: PCT/US2008/086624
§ 371 (c)(1),
(2), (4) Date: Sep. 29, 2010

(87) PCT Pub. No.: WO2009/079383
PCT Pub. Date: Jun. 25, 2009

(65) Prior Publication Data
US 2011/0021966 A1    Jan. 27, 2011

Related U.S. Application Data

(60) Provisional application No. 61/014,065, filed on Dec. 16, 2007, provisional application No. 61/014,005, filed on Dec. 14, 2007.

(51) Int. Cl.
*A61M 37/00* (2006.01)
(52) U.S. Cl.
USPC .................. 604/6.08; 604/6.03; 604/4.01
(58) Field of Classification Search
USPC ............................... 604/4.01–6.16
See application file for complete search history.

(56) References Cited

U.S. PATENT DOCUMENTS

| | | | |
|---|---|---|---|
| 4,390,432 A * | 6/1983 | Takeguchi et al. | 210/615 |
| 4,765,899 A | 8/1988 | Wells et al. | |
| 4,921,473 A | 5/1990 | Lee et al. | |
| 7,588,550 B2 | 9/2009 | Leonard et al. | |
| 7,727,399 B2 | 6/2010 | Leonard et al. | |
| 7,850,633 B2 | 12/2010 | Leonard et al. | |
| 7,850,634 B2 * | 12/2010 | Briggs | 604/6.08 |
| 8,021,318 B2 | 9/2011 | Leonard et al. | |
| 8,083,706 B2 | 12/2011 | Leonard et al. | |
| 8,092,684 B2 | 1/2012 | Leonard et al. | |

(Continued)

FOREIGN PATENT DOCUMENTS

| | | |
|---|---|---|
| WO | WO 2004/082796 | 9/2004 |
| WO | WO 2006/124431 | 11/2006 |
| WO | WO 2007/137245 | 11/2007 |

OTHER PUBLICATIONS

Goldsmith, Harry L., Margination of Leukocytes in Blood Flow through Small Tubes, 1984, Microvascular Research; 27: 204-222.*

(Continued)

*Primary Examiner* — Philip R Wiest
*Assistant Examiner* — Benjamin Klein
(74) *Attorney, Agent, or Firm* — Miles & Stockbridge P.C.; Mark A. Catan

(57) ABSTRACT

A blood treatment device provides a photopheresis treatment using a microfluidic separation channel to separate blood components into layers The layering caused by laminar flow in the microfluidic separation channel allows light to be projected through plasma onto leukocytes without hindrance by erythrocytes.

18 Claims, 8 Drawing Sheets

(56) References Cited

U.S. PATENT DOCUMENTS

| | | |
|---|---|---|
| 8,097,153 B2 | 1/2012 | Leonard et al. |
| 8,097,162 B2 | 1/2012 | Leonard et al. |
| 2004/0225249 A1 | 11/2004 | Leonard et al. |
| 2006/0076295 A1 | 4/2006 | Leonard et al. |
| 2008/0009780 A1 | 1/2008 | Leonard et al. |
| 2009/0139931 A1 | 6/2009 | Leonard et al. |
| 2009/0292234 A1 | 11/2009 | Leonard et al. |
| 2010/0004578 A1 | 1/2010 | Leonard et al. |
| 2010/0198131 A1 | 8/2010 | Leonard et al. |
| 2011/0056884 A1 | 3/2011 | Leonard et al. |
| 2011/0062083 A1 | 3/2011 | Leonard et al. |
| 2011/0066097 A1 | 3/2011 | Leonard et al. |
| 2011/0105982 A1 | 5/2011 | Leonard et al. |

OTHER PUBLICATIONS

Higuchi et al., "Peripheral blood cell separation through surface-modified polyurethane membranes," *Journal of Biomedical Materials Research—Part A*, 2004, 68A(1): pp. 34-42.

Kyritsis, Socrates, "Ultraviolet irradiation of white blood cells in flowing whole blood," Master's Thesis, Department of Chemical Engineering and Applied Chemistry, Columbia University, New York, NY, Oct. 1992.

Leonard et al., "Dialysis without Membranes: How and Why?," Blood Purification, 2004, 22 (1):pp. 92-100.

Leonard et al., "Membraneless Dialysis—Is it Possible?" Contributions to Nephrology, 2005, 149: pp. 343-353.

\* cited by examiner

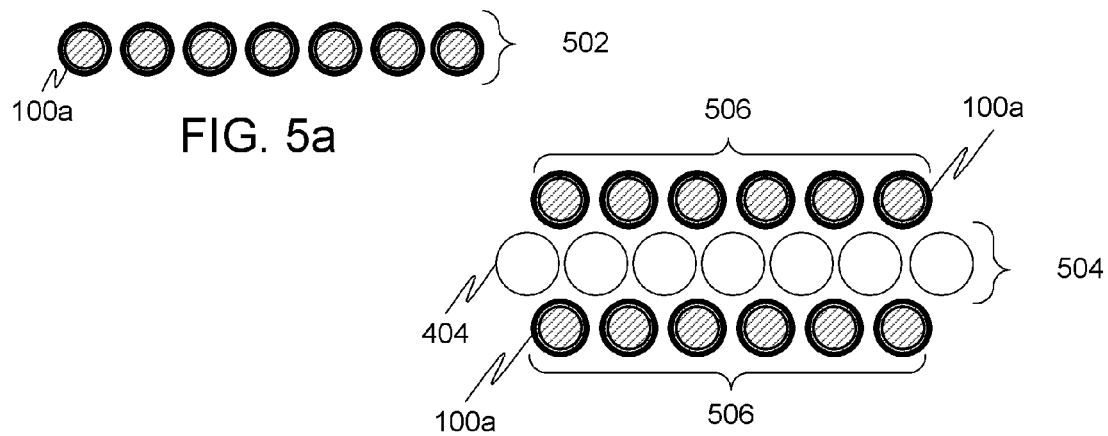
FIG. 5a
FIG. 5b
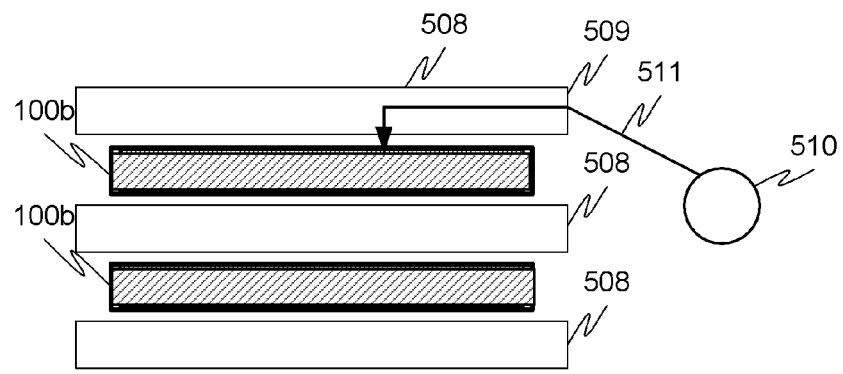
FIG. 5c
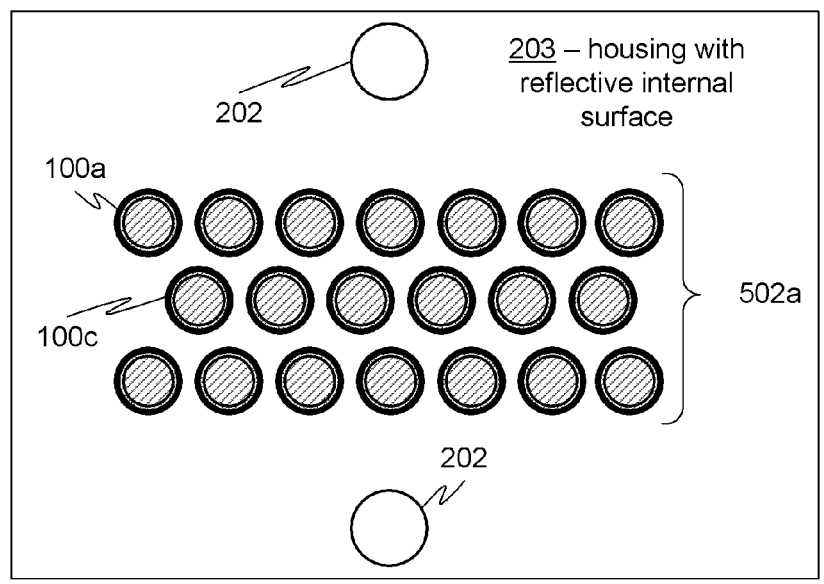
FIG. 5d

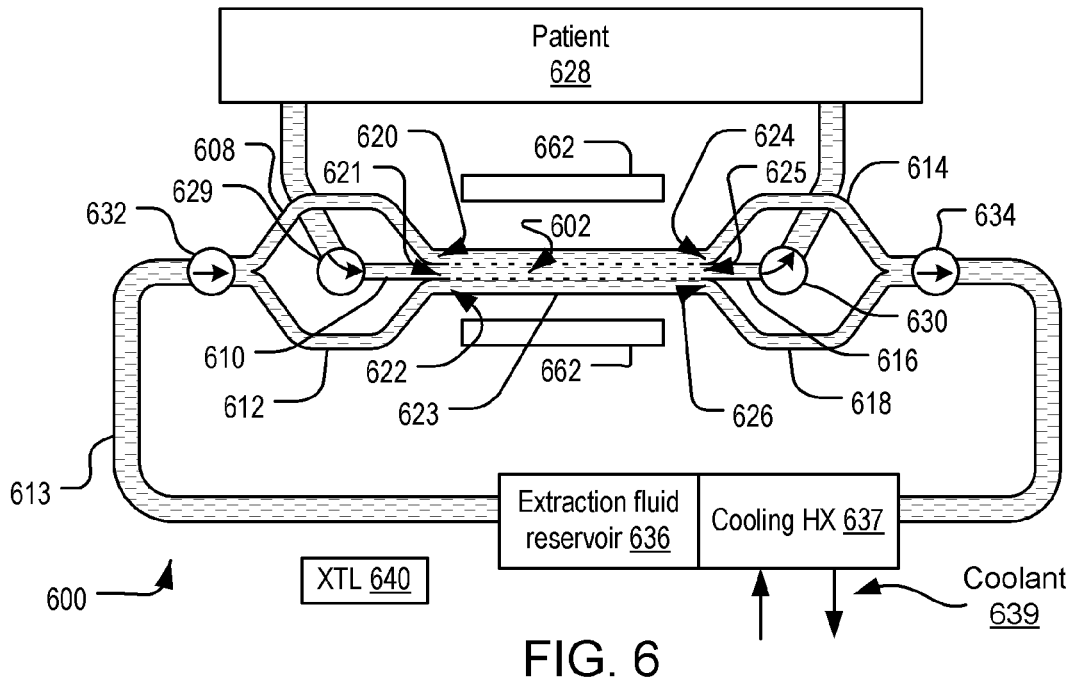
FIG. 6
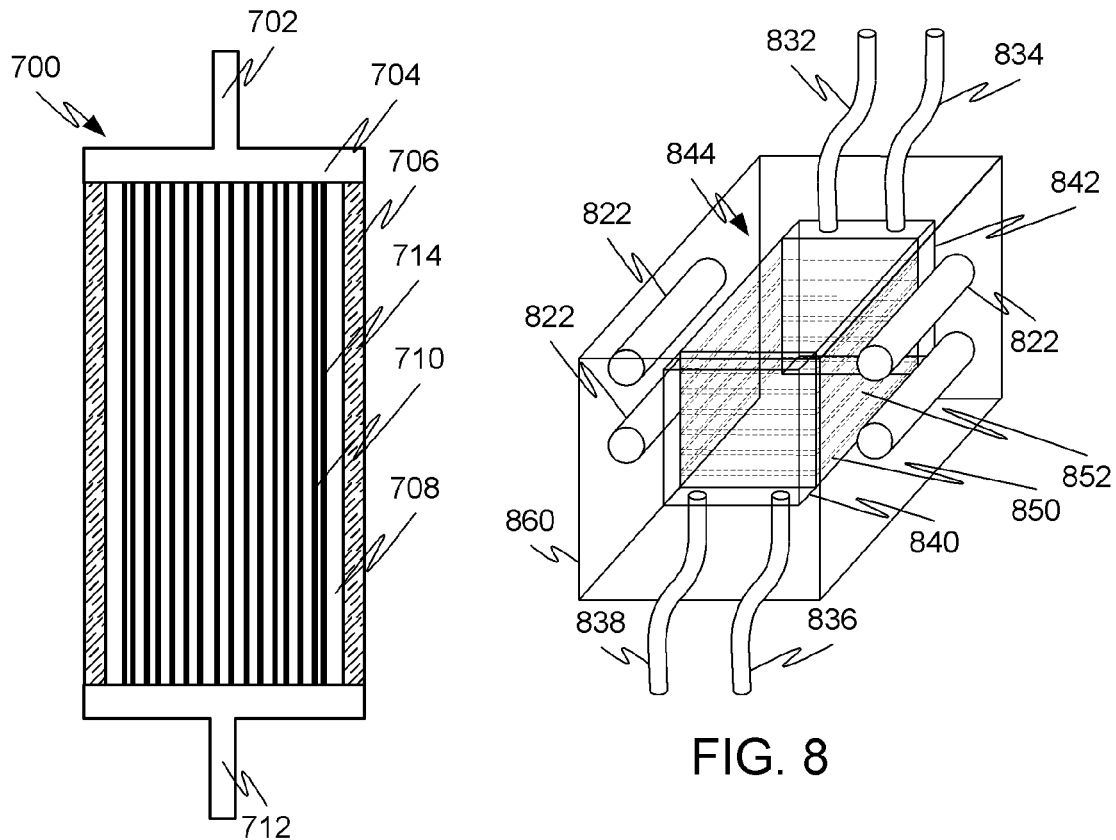
FIG. 7
FIG. 8

SYSTEMS, METHODS, AND DEVICES FOR BLOOD TREATMENT

CROSS-REFERENCE TO RELATED APPLICATIONS

This application is a national stage application of International Application No. PCT/US08/86624, filed on Dec. 12, 2008, currently pending, which claims the benefit of U.S. Provisional Application No. 61/014,005, filed Dec. 14, 2007, now expired, and U.S. Provisional Application No. 61/014,065, filed Dec. 16, 2007, now expired, all of which are hereby incorporated by reference herein in their entireties.

STATEMENT REGARDING FEDERALLY-SPONSORED RESEARCH

This invention was made with U.S. government support under RO1 HL038306 awarded by the National Institutes of Health—National Heart, Lung, and Blood Institute. The U.S. government has certain rights in the invention.

BACKGROUND

The present application relates generally to the extracorporeal treatment of sample fluid, and, more particularly, to the extracorporeal photopheresis of blood, or a component thereof, using a microfluidic device.

Extracorporeal photopheresis is a form of apheresis therapy that involves light activated treatment of circulating blood cells outside the body. This modality is directed to circulating leukocytes (i.e., white blood cells) and has been applied to the relatively rare neoplasm, cutaneous T-cell lymphoma (CTCL). The modality involves systemic administration of a light-activatable drug, 8-methoxypsoralen, also referred to as psoralen. The drug binds to the DNA of leukocytes, whereas erythrocytes (i.e., red blood cells) and platelets, which both contain no DNA, are unaffected by the drug. A unit of blood (~500 ml) is removed from circulation within the body via an intravenous (IV) line placed in a patient. Using a centrifuge, the leukocytes are separated from the other components of the blood and irradiated. This separation is necessary because the vastly greater number of erythrocytes would shield the leukocytes if whole blood were directly irradiated. Also, it can be undesirable to irradiate the erythrocytes for certain treatments.

The leukocytes can be irradiated with ultra-violet (UV) light at approximately 340 nm. The leukocytes are then recombined with the blood and returned to the body. The UV light causes a reaction of the psoralen to cross-link the DNA of the leukocytes and thereby damage the genetic information of the cell. The damaged cells induce an immune response that can result in the suppression of malignant T-cell production.

The above-discussed technique involves the removal of a unit of blood of ~500 ml for processing at any one time. To treat a sufficient blood volume for an effective response, many cycles of exsanguination and reinfusion over a period of a couple days are typically necessary. However, this extended treatment duration may not be optimal for a desired immune response. Further, such systems can require precise controls for the separation, irradiation, and reintroduction of leukocytes. Applications to additional modalities have thus been impeded by the expense, size, technical demands and inconvenience to the patient imposed by equipment for extracorporeal photopheresis.

SUMMARY

Systems, methods, and devices for the treatment of blood are disclosed herein. A blood treatment device can provide photopheresis treatment by separating flowing blood into constituent layers. For example, blood components can be separated into layers in a separation channel. This layering can be caused by laminar flow in the separation channel. This layering can allow light from a therapeutic light source to be projected on some layers without hindrance by components in other layers.

For example, blood components can separate into layers with erythrocytes in the center of a separation channel and plasma at the margins of the separation channel during laminar flow in small channels. Leukocytes tend to settle in a thin intermediate layer between these two layers. This behavior is manifested when blood flows through very small channels at low flow rates, for example, tubes of sub-millimeter size at shear rates less than 100 sec$^{-1}$. This behavior can occur in cylindrical channels as well as rectilinear channels. Thus, light from a therapeutic light source can be projected through plasma onto leukocytes without hindrance by erythrocytes.

BRIEF DESCRIPTION OF DRAWINGS

Where appropriate, like elements in the figures have been identified by the same reference number. Unless otherwise noted, the drawings have not been drawn to scale.

FIG. 5a shows a configuration of circular microchannels in an array.

FIG. 5b shows a configuration of circular microchannels in a two-dimensional array coupled to a corresponding array of light pipes.

FIG. 5c shows a configuration of rectilinear microchannels in an array coupled to a corresponding array of light plates.

FIG. 5d shows a configuration of circular microchannels in two-dimensional array within a reflective housing.

FIG. 6 shows an extracorporeal photopheresis microfluidic device with sheathing fluid flow paths.

FIG. 7 shows a dialyzer-based extracorporeal photopheresis microfluidic device.

FIG. 8 shows a perspective view of a photopheresis device with illumination sources, multiple separation channels, and light pipe layers between the channels.

DETAILED DESCRIPTION

Figures 1A, 1B:
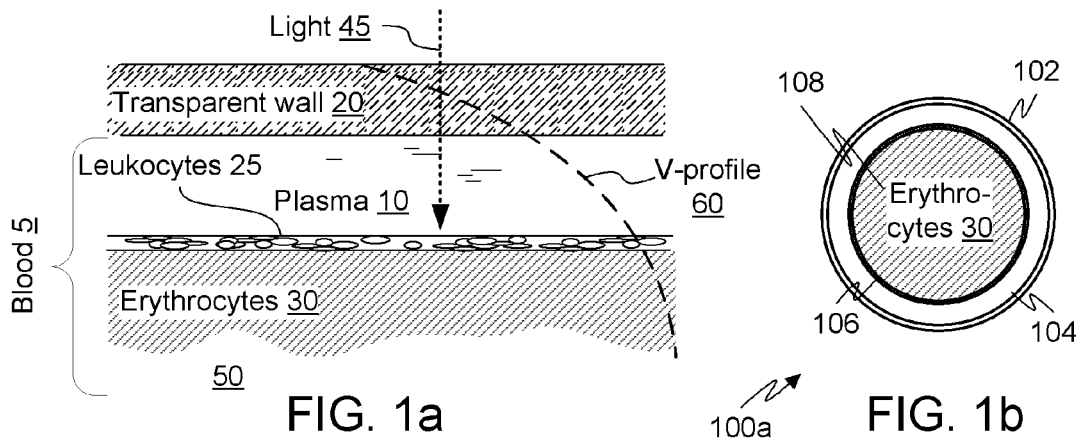
FIG. 1a illustrates a microfluidic flow channel in a longitudinal section for purposes of describing features of a photopheresis device.
FIG. 1b is a figurative diagram of a cross-section of a layered flow pattern in a circular microfluidic separation channel.

An example of a blood treatment device has (i.e., comprises) a separation channel configured to connect to a living animal and to permit the passage of blood therethrough at a flow rate that causes blood to arrange approximately in layers. The layers include (i.e., comprise) a first, plasma-rich layer on one side, a second, erythrocyte-rich layer opposite the first layer and a third, leukocyte-rich layer between the first and second layers. The layers can be formed as a result of differential shear rates of the flow in the microfluidic separation channel. The effect exploited in such examples is characterized as margination of leukocytes, indicating the tendency of leukocytes to move toward higher shear margins of a laminar flow with erythrocytes tending to move toward the lower shear central region of the laminar flow. The blood treatment device has connectors on blood lines connecting the separation channel and configured for connection to a patient access. A therapeutic light source is positioned to illuminate the third layer by transmitting light through the first layer.

In a variation, the separation channel has at least one transparent wall through which light from the light source is transmitted. The light source can be configured to generate light with a substantial component in the wavelength range of 200-400 nm. The separation channel can have a minimum internal dimension of less than 200 μm. The separation channel can be rectilinear with a cross-section whose aspect ratio is greater than 10, for example, greater than 50. The separation channel can include multiple subchannels so as to form a compact configuration. The device can further include a pump configured to flow blood through the separation channel at a rate of 30 ml/min.

Another variation of a blood treatment device has a housing enclosing a flat laminar separation channel with inlet and outlet ports connected to patient connection lines. A blood pump in the housing is configured to pump blood through the separation channel at a rate that causes blood to arrange approximately in layers with a first, plasma-rich layer on one side, a second, erythrocyte-rich layer opposite the first layer, and a third, leukocyte-rich layer between the first and second layers. The housing encloses a therapeutic light source positioned to illuminate leukocytes present in the third layer. The light source can be positioned to illuminate the separation channel and transmit light through the first layer to the third layer.

In another variation, a leukocyte receiving channel is connected between the separation channel and one of the patient connection lines to receive at least a fraction of the leukocyte-rich layer and return the fraction to at least one of the patient connection lines such that the fraction can be returned to a patient. The separation channel can have at least one transparent wall through which light from the light source is transmitted. The light source can be configured to generate light with a substantial component in the wavelength range of 200-400 nm. The separation channel can have a minimum internal dimension of less than 200 μm. The separation channel can be rectilinear with a cross-section whose aspect ratio is greater than 10. The separation channel can include multiple rectilinear channels each having a cross-section whose aspect ratio is greater than 50. The blood pump can be configured to flow blood through the separation channel at a rate of 30 ml/min. A method of performing photopheresis can include increasing the concentration of leukocytes in a living animal's blood by creating a flow of the blood that generates a shear profile that causes leukocytes to be concentrated in a fraction of the flow, illuminating the leukocytes in the fraction of the flow, and returning the illuminated leukocytes to the living animal. In the method, the flow can be laminar and can have a minimum cross-stream dimension of less than 200 μm. The illuminating can include generating light having a significant portion of its energy in the 200-400 nm wavelength range. The illuminating can include shining light on transparent walls of a channel containing the flow.

As shown in FIG. 1a, blood 5 passes in laminar flow through a separation channel 50 at such velocity and channel radius or depth, depending on the configuration, that leukocytes 25 and erythrocytes 30 settle into respective layers with only plasma 10 remaining at the margins of the flow. This layering is driven by the differences in shear rates attending the laminar velocity profile 60 (the illustration is not adjusted for viscosity differences resulting from the layer and is merely figurative). The separation channel can have dimensions that assure laminar flow conditions are maintained even under conditions of normal use.

The walls 20 of the separation channel can admit light 45, for example, by being transparent to wavelengths of light 45. In this way, the layering effect, with leukocytes 25 concentrated at the margins of the flow, permits light to strike the leukocytes 25 without being blocked by the erythrocytes 30. The separation channel can be provided in a microfluidic device according to various examples described herein.

Figure 1C:
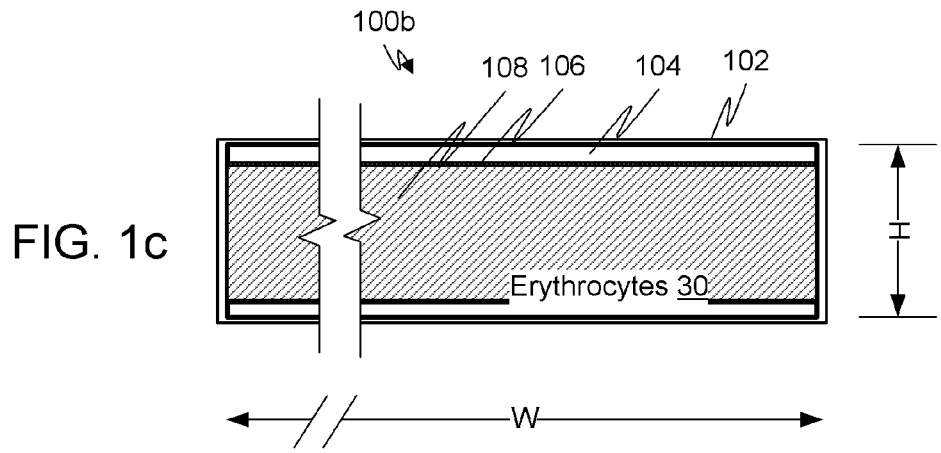
FIG. 1c is a figurative diagram of a cross-section of a layered flow pattern in a rectilinear microfluidic separation channel.

FIG. 1b illustrates a cylindrical microfluidic separation channel 100a or capillary in which the layering effect is achieved and FIG. 1c shows the same layering effect in a rectilinear separation microchannel 100b, which can have a wide flat rectangular cross-section. In a light-transmitting separation channel, the wide flat configuration exposes a large area of leukocytes 106 to light incident on the major surface of the separation channel. Useful devices can be made with cylindrical separation channels 100a as well as the rectilinear separation channel 100b. For example, cylindrical channels can be arrayed to expose a large surface layer of leukocytes to incident light as also discussed by way of various examples, below.

In the cylindrical channel 100a, the diameter of the flow can be, for example, of the order of 100 μm. In the rectilinear channel 100b, the cross-section has a width, W, and a height, H, both of which are taken in a plane perpendicular to the direction of flow. In an embodiment, the rectilinear microchannel is a narrow channel with a width much greater than the height (e.g., W>50*H) to provide a large area. The height H can be, for example, of the order of 100 μm. The height can be more or less than the above dimensions depending on other conditions, such as flow rate, mechanical stresses (e.g., vibration, bending, etc.) of the channel. For example, a channel of 200 μm depth can perform effectively and a channel much smaller than 100 μm depth can also be effective.

Figures 2A, 2B:
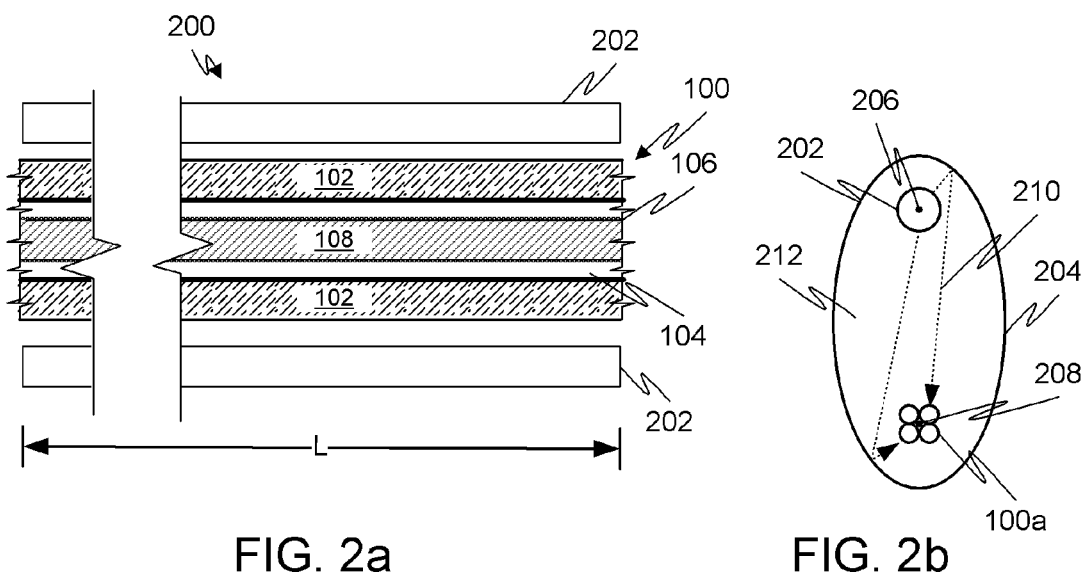
FIG. 2a shows a configuration for an extracorporeal photopheresis microfluidic device.
FIG. 2b shows a configuration of an optical setup for illuminating a bundle of circular microfluidic separation channels.

The above-described flow configurations illustrated in FIGS. 1b and 1c can be used to illuminate leukocytes using an external therapeutic light source. Referring to FIG. 2a, a device 200 can be configured with a therapeutic light source 202, such as an elongate gas-emission lamp, and a transparent separation channel 100 with suitable size and flow rate, such that light passes through both the channel walls and plasma 104 so as to strike the leukocyte layer 106 without being attenuated substantially by the erythrocyte layer 108. The device 200 can be housed in a light-shielding housing with a reflective interior surface (not shown). Therapeutic light source 202 can be positioned to illuminate the leukocytes 106 over a length, L, chosen to provide a medically effective dosage of light.

A medically effective quantity of psoralen can be provided in the blood prior to introduction in the separation channel 200. For example, the therapeutic light sources 202 can emit wavelengths within a wavelength range, for example, from about 200-400 nm. The light sources can emit a wavelength in the 320-400 nm range, for example, at a wavelength of 340 nm. The above examples of wavelengths and wavelength ranges are merely exemplary. Other wavelengths and ranges can be selected for the light source according to desired treatment type and/or effect. Further, a blood flow of, for example, 30 ml/min can be provided through the channel 200, which can provide the equivalent to treating approximately four transfusion units of blood per hour by the discussed blood centrifugation technique. These flow rate figures are merely illustrative, as higher or lower flow rates can also be employed in any of the examples discussed herein. For example, the flow rate can be between two transfusion units per hour and eight transfusion units per hour. The height, H, of the microfluidic separation channel can be on the order of 120 µm, for example. The microfluidic separation channel can have a width, W, more than ten (10) times greater than H and, for example, more than fifty (50) times greater than H.

Separation channels of other shapes can also be used, as should be evident from the present discussion. For example, a large exposed area can be achieved in the annular gap between two cylinders with a radial gap on the order of 120 µm. A flat channel could be rolled into a scroll shape to achieve compactness without changing the fundamental flow properties. Flattened oval, elliptical, or cylindrical separation channels can also be used. Light can be admitted on all sides of the channel so that an effective quantity of leukocytes are irradiated using a minimally-sized channel.

In an example, assuming a channel height, H, of 120 µm and processing rate of 30 ml/min, a desired extracorporeal volume in the illuminated portion of rectilinear separation channel would be 5 ml. With a 10 second blood residence time, the en face surface area of the transparent separation channel would be approximately 420 cm$^2$ (or 840 cm$^2$ total, since both sides of the flowing blood would be illuminated). Based on the channel height, H, this volume requires an en face area of 5/0.012 or 417 cm$^2$. The shear rate can be calculated as 6*(average velocity)/(layer thickness). Assuming a wall shear rate of 50 sec$^{-1}$, which is well below that required for margination, the average velocity of the blood flow becomes 0.10 cm/sec for the above configuration. Thus, for a 10 second residence time, a flow path length, L, of 100 cm would be necessary. To achieve the necessary en face area of 417 cm$^2$ over the 100 cm length, the separation channel would have a width, W, of 4.17 cm.

Practical realizations of this path length could be achieved as, for example, with 5 segments, each 20 cm long between two transparent surfaces, each with an effective area of 417 cm$^2$. A lower shear rate would aid margination and reduce the overall length of the flow path but make it wider. As discussed with reference to various examples described herein, multiple narrow separation subchannels can be arranged to form a stacked configuration that has the same effect as a wider shorter separation channel. A shorter residence time at a fixed shear rate would decrease the area. It will be understood that the dimensions provided above are for purposes of illustration only.

In addition to a lamp, other optical components can be provided to enhance the uniformity of illumination of leukocytes and/or the efficiency of light utilization. In embodiments, the arrangement of therapeutic light source(s) and optical component(s) can be used to optimize uniformity of light distribution on the surface of leukocyte layers. In one or more other embodiments, the arrangement of therapeutic light source(s) and optical component(s) can be used to optimize the efficiency of light distribution on the surface of leukocyte layer, that is, to reduce the total amount of wasted light, thereby permitting a minimally-sized power supply and light generator. This can achieve the advantage of reducing the size and weight of a treatment device as a result of having a minimally smaller power supply and light source. To achieve these results, as discussed in terms of examples below, light from a source can be directed with a minimum number of optical transmission and/or reflection stages. In addition, or alternatively, light can be directed in a uniform intensity pattern toward the leukocyte surface or surfaces. The light can be directed to take into account refraction of the channel walls and plasma.

For example, FIG. 2b employs a reflector to direct all the light from an elongate therapeutic light source 202 to a target array of one or more separation channels 100a. A cylinder having an elliptical cross-section defines a reflector 204 that directs light 210, 212 from the source 202, positioned at one focus 206, to one or more microfluidic separation channels 100a located at the other focus 208. The channels 100a can be any in number. Although four separation channels are shown, fewer or additional microfluidic separation channels can be provided. For example, the channels can be arranged in a circular array so that no single one shades another completely.

Figure 2C:
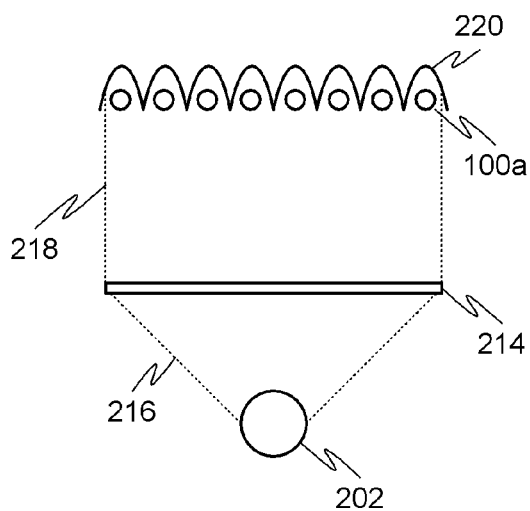
FIG. 2c shows a configuration of an optical setup for illuminating an array of microfluidic separation channels.

Referring to FIG. 2c, in another example, light 216 from therapeutic source 202 is directed into collimated beams by optical element 214, which can be, for example, a Fresnel lens, a regular lens, lens system, or any other focusing element. Although not shown, the source 202 can include an optical component such as a reflector to direct light toward the optical element 214 (for example, similar to the reflector 222 illustrated in FIG. 2f, which directs light from source 202a). The collimated rays 218 are directed at an array of circular microfluidic separation channels 100a with reflectors 220 positioned adjacent the channels to focus the collimated radiation onto each microfluidic separation channel. Although the embodiment shown has a series of reflectors 220 with a parabolic, elliptical, or trough shape, a flat reflector with a specular or diffuse reflecting surface can be used. Alternatively, although not illustrated, the reflectors 220 and separation channels 100a can be arranged in a cylindrical array about the source 202 with or without an intermediate optical element 214.

Figure 2D:
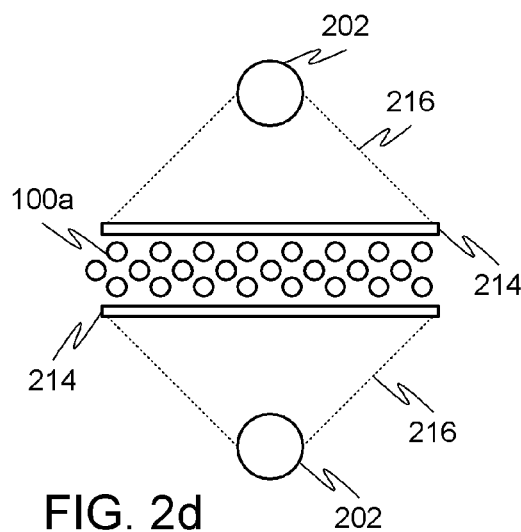
FIG. 2d shows another configuration of an optical setup for illuminating an array of microfluidic separation channels.
Figure 2E:
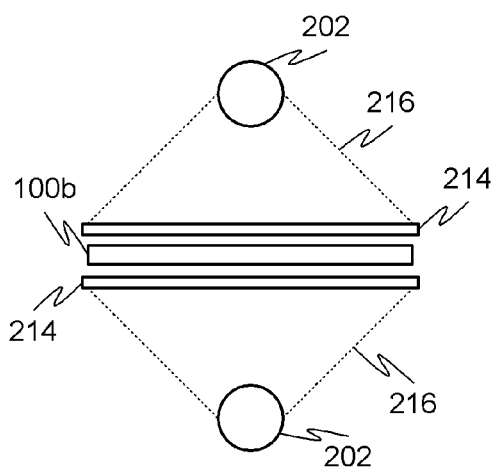
FIG. 2e shows a configuration of an optical setup for illuminating a rectilinear microfluidic separation channel.
Figure 2F:
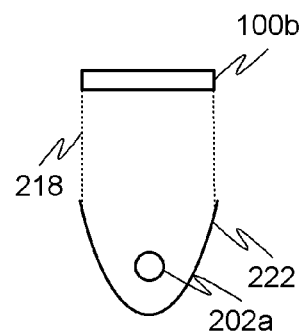
FIG. 2f shows another configuration of an optical setup for illuminating a rectilinear microfluidic separation channel.

In another example shown in FIG. 2d, light 216 from a pair of therapeutic light sources 202 positioned on opposite sides of microfluidic separation channels 100a is collimated by respective optical elements 214 to illuminate microfluidic separation channels 100a uniformly over the width thereof. In another example, shown in FIG. 2e, the same arrangement of light sources 202 and optical elements 214 illuminate a flat channel 100b carrying a thin sheet flow. In another embodiment, a parabolic reflector 222 directs light in a collimated beam at a flat laminar separation channel 100b. Other optical systems and arrangements can of course be employed, as would be evident to one of ordinary skill in the applicable arts, in accordance with the goal of optimizing illumination of the microfluidic separation channels. Further, although FIGS. 2b-2f illustrate one or more microfluidic separation channels with certain cross-sections, separation channels with other cross-sections and in varying number can be used in otherwise similar examples.

Figure 3A:
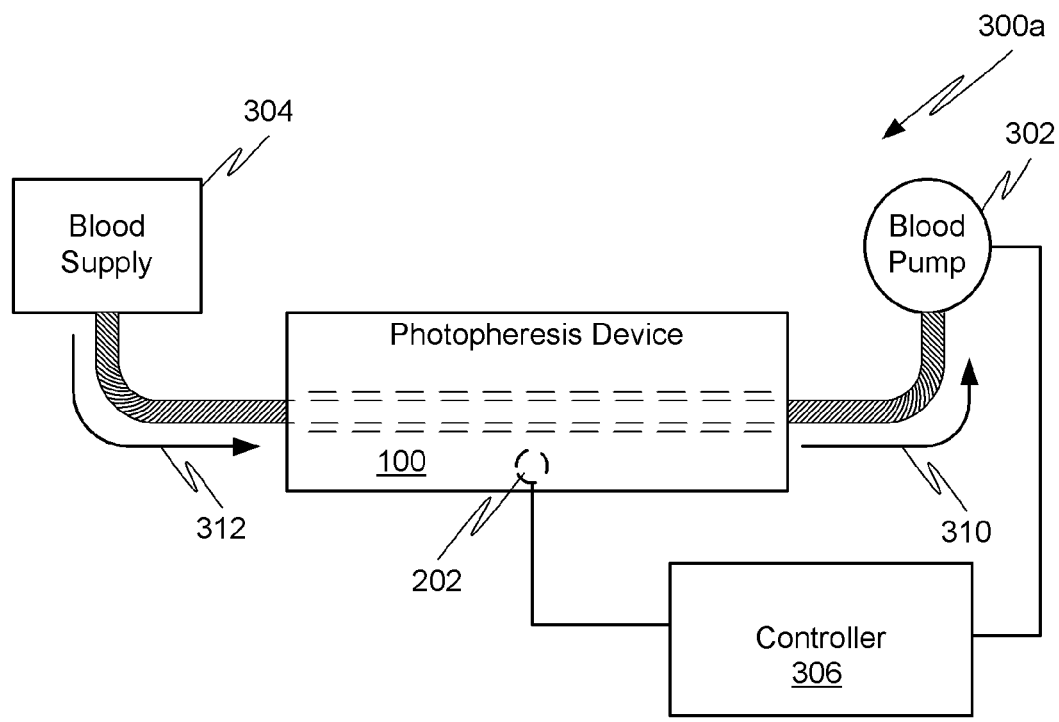
FIG. 3a shows a simplified block diagram of a configuration for an extracorporeal photopheresis microfluidic device.

Referring now to FIG. 3a, any of the foregoing extracorporeal photopheresis microfluidic devices can be employed in a blood processing system 300a for treating blood of a patient. System 300a includes a blood supply 304 and a blood pump 302 configured to pump blood through the microfluidic separation channel 100 so as to be illuminated by therapeutic light source 202. Blood pump 302 removes blood from the microfluidic separation channel 100 through the outlet of the device in the direction shown by arrow 310. The blood pump 302 could be positioned in a pull configuration as shown downstream of the photopheresis device 100 or in a push configuration, not shown, but located upstream of the photopheresis device, for example, between the blood supply 304 and the extracorporeal photopheresis device 100. The therapeutic light source and separation channel can be housed in a light-trapping housing to prevent light from escaping. A controller 306 can control operation of the system 300a, including, but not limited to, the operation of the light source(s) 202 and the operation of one or more blood pumps 302. Although not shown in the figures, sensors can be used to provide feedback on flow rate in conjunction with the controller 306.

Figure 3B:
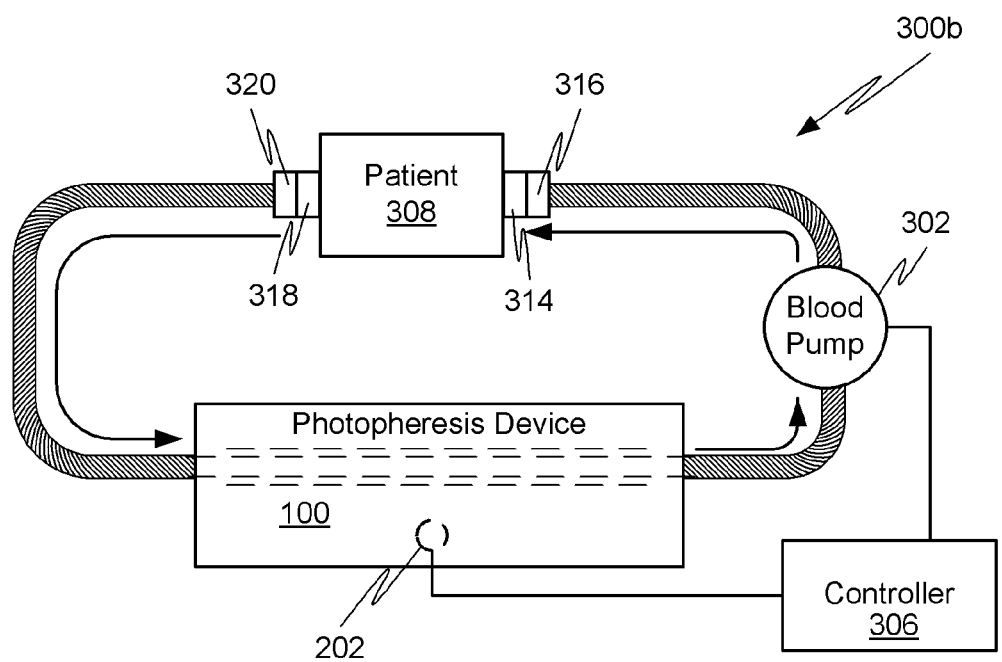
FIG. 3b shows a simplified block diagram of a configuration for an extracorporeal photopheresis microfluidic device.

In another example, blood processing system 300a can be configured for integration with a recirculating blood supply system for use with a patient, such as a living person or animal. In a recirculating blood treatment system 300b, as shown in FIG. 3b, a separation channel can be connected to a patient 308 using connectors 316 and 320 on blood lines coupled to respective patient accesses 314 and 318. Although shown separately in the illustration of FIG. 3b, connectors and/or accesses can be integrated. For example, connectors 316 and 320 can be integrated into a single connector with inlet and outlet lines. Similarly, patient accesses 314 and 318 can be combined into a single patient access with inlet and outlet portions. In the recirculating blood treatment system 300b, blood can be removed from a patient 308, can be subjected to treatment in the microfluidic separation channel 100 within the blood flow path, and can be returned to the patient 308, thereby forming a continuous extracorporeal blood circuit. In a small-sized wearable system, blood can be treated continuously at relatively low rates to achieve a desired clinical outcome.

Any necessary light-sensitive drugs can be introduced into the blood supply 304 by addition to a blood reservoir or through ingestion by the living person or animal. Further, the light-sensitive drugs can be introduced to the living person or animal by other means known in the art, such as by injection or intravenously. Alternatively, the light-sensitive drugs can also be introduced into the blood flow within or prior to the separation channel 100 itself.

Components of blood processing system 300a or blood processing system 300b can be integrated as appropriate to provide a unitary portable system. Further, the disclosed examples of the blood processing system can be made sufficiently integrated and compact so as to be wearable by a living person or other animal, for example. In addition, the disclosed examples of the blood processing system can be made sufficiently integrated and compact so as to be at least partly implantable within a living person or animal, for example. The blood processing system can have a fully implanted blood channel and light source with external controls and power source or it can be entirely implanted or completely external. All of the devices and systems described herein, except where explicitly excluded, can be implanted devices.

Figure 4A:
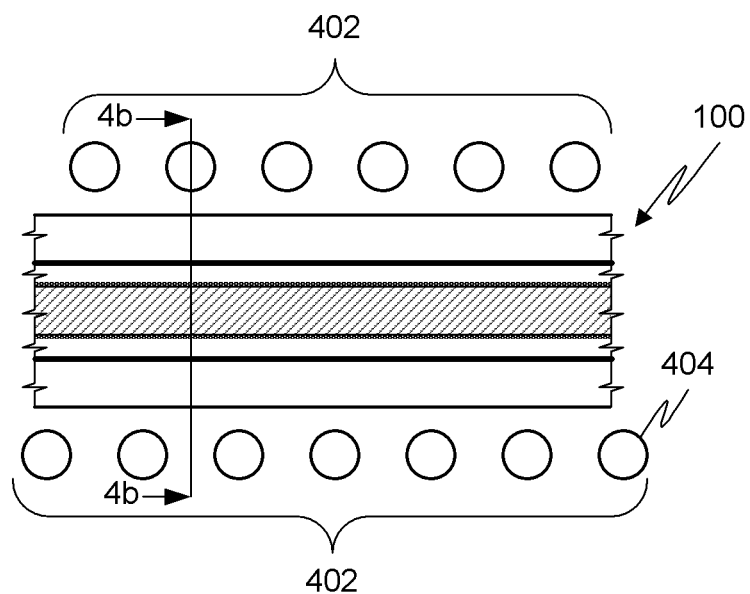
FIG. 4a shows a cross-section of a slit-type microfluidic separation channel and a configuration of an array of light pipe sources. Blood flow is in the direction perpendicular to the plane of the page.
Figure 4B:
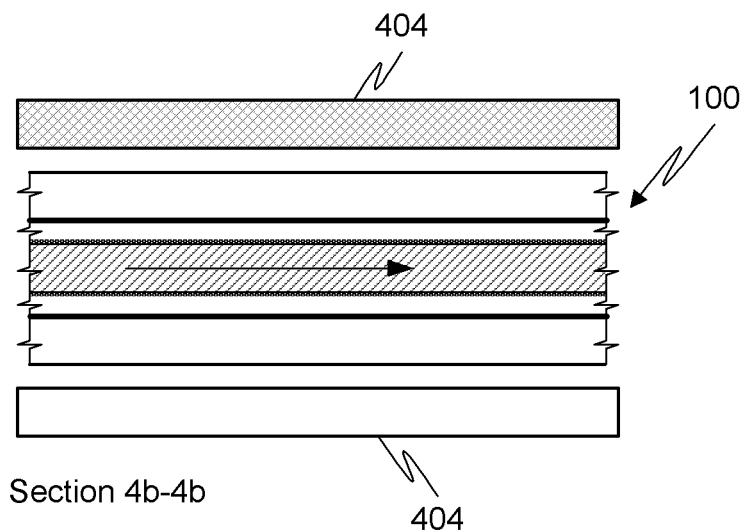
FIG. 4b shows a side view along section 4b-4b of FIG. 4a. Blood flow is in the direction indicated by the arrow.

FIGS. 4a and 4b illustrate the use of a light distribution device such as a light pipe or fiber-optic bundle in conjunction with a therapeutic light source to distribute light to an extracorporeal photopheresis microfluidic separation channel 100. Illumination system 402 has an array of light pipes 404 configured to distribute light uniformly over their lengths, for example, by using a thin film incorporating microscopic prisms, such as a light pipe manufactured by 3M Corporation. An external lamp (not shown) disposed at the end of the light pipe 404 provides the requisite illumination. Light is transmitted down the length of the pipe and becomes uniformly distributed external to the light pipe along its length. By using an array of light pipes 404 in the illumination system 402, UV light can thus be delivered uniformly along the entire length, L, as well as the width, W, of the microfluidic photopheresis device 100.

Other light delivery devices and techniques can also be employed in the configurations illustrated in FIGS. 4a and 4b. For example, solid state light source can be used. In such an example, the solid state light sources can be sufficiently compact so as to be arranged in thin arrays. Thus, in place of elements 404 in FIGS. 4a and 4b, solid state light sources can be provided to serve as therapeutic light sources. Any other light pipe or light tube known in the art can also be employed, such as light tubes incorporating fluorescent material for wavelength conversion. Further, the light pipe is not limited to the circular cross-section as shown in FIGS. 4a and 4b. Instead, other cross-sections, such as a rectilinear cross-section light guide, can be used. It will also be understood that the number of light pipes 404 shown in FIGS. 4a and 4b is merely for illustrative purposes. Fewer or additional light pipes, regardless of cross-sectional shape, can be employed.

The requisite microfluidic separation channel areas can be achieved by combinations of channel length, width, and number according to the principles of the present disclosure. It is shown herein that the competing requirements of small height (to allow margination), short length (to avoid excessive pressure drop), and practical limitations on width of a single device, which suggests the need to array them in parallel, side-by-side, or in a stack, can be satisfied in practical microfluidic devices. FIGS. 5a-5d address these embodiments of the extracorporeal photopheresis microfluidic device.

FIG. 5a shows an array of multiple circular microfluidic separation channels 100a forming a one-dimensional array 502. Note that a source of electromagnetic radiation, such as a UV light source, is presumed, though not shown, in FIG. 5a. The multiple parallel separation channels allow for a more compact configuration. Although a flat array is shown, a multilayered or staggered array (forming a honeycomb pattern in cross-section) could be employed as shown in FIG. 5d. In FIG. 5d, light sources 202 illuminate an array of transparent separation channels (or capillaries) 502a inside a housing 203 with a reflective internal surface. Separation channels (or capillaries) 100c, which are partially surrounded by separation channels (or capillaries) 100a, can still receive light directly from the therapeutic light source, or reflected light from the housing, depending on the packing arrangement. FIG. 5b shows an alternative embodiment for a configuration of circular microfluidic separation channels 100a as a two-layer array 506. Interposed between the two rows of microfluidic separation channels 100a is an array 504 of light pipes

404. Alternatively, the elements 404 can be compact therapeutic light sources, such as solid state light sources. The light pipes 404 can receive light at their longitudinal ends and can be configured such that they convey this light radially away along their lengths to illuminate the capillaries 100*a*. By using light pipes in this manner, a compact arrangement can be achieved.

FIG. 5*c* shows another embodiment having separation channels 100*b* of rectilinear cross-section. Interposed between each pair of microfluidic separation channel 100*b* can be a plate-shaped light conductor or light pipe, hereafter referred to as a light plate 508. The light plate 508 functions substantially similar to the light pipe 404, but is formed having a rectilinear configuration so as to provide illumination over a larger surface area. Light 511 from a therapeutic light source 510 enters one or more edges 509 of the light plates 508 and is directed along the plate 508 until it is directed toward the channel 100*b*. The single beam 511 is representative, of course, of many light beams such that the channels 100*b* are effectively bathed in light. Although not shown, the separation channels can be connected to manifolds or headers at each end to distribute flow from a single feed and gather it to a single outlet. Such headers can be created using potting, three-dimensional dot-matrix printing, molding, lithographic and/or laminating techniques.

The configurations shown in FIGS. 5*a*-5*d* are exemplary in nature. Accordingly, any combination of microfluidic separation channels, therapeutic light sources, and arrays thereof can be constructed without departing from the spirit and scope of the present disclosure. Further, it is envisioned that an array of therapeutic light sources, which can be light pipes or other types of therapeutic light sources, can be symmetrically arranged around each microfluidic separation channel so as to provide uniform illumination around the periphery thereof.

Further, the number of therapeutic light sources can vary as necessary to allow for sufficient illumination of the leukocytes over the entire length of the channel(s). Also, any light source capable of providing the necessary wavelengths of light could be used. This includes light emitting diodes (LED), superluminescent diodes (SLD), laser diodes (LD), metal halide and mercury vapor lamps, and other sources commonly employed in the art. The light sources can include integral optics, filters, and cooling components.

FIG. 6 illustrates another embodiment of an extracorporeal photopheresis microfluidic device 600. A therapeutic light source 662 illuminates a separation channel 623 but the blood flow is sheathed by an osmotically blood-normal sheathing fluid flow, as described in International Patent Application (designating the U.S.) No. PCT/US06/18008, filed May 9, 2006, entitled "Systems and Methods of Blood Based Therapies Having a Microfluidic Membraneless Exchange Device," which is hereby incorporated by reference in its entirety. All of the teachings of this incorporated reference relating to microfluidic separation channels and systems are relevant to any and all embodiments of the present disclosure, except that the need to refresh sheathing fluid in the disclosed examples of the incorporated reference is not necessarily essential for embodiments herein that do not cleanse blood. Thus, embodiments of the incorporated reference, in which sheathing fluid is recirculated in a sheathing fluid channel 613, need not necessarily pass through an ultrafilter or other type of secondary processor as taught in the incorporated reference. However, as mentioned below, some embodiments of a photopheresis device can also perform a blood cleansing function simultaneously.

In FIG. 6, sheathing fluid can provide diminished risk of adverse reaction of the blood with the artificial surfaces 623 of the separation channel 602. The sheathing fluid can also be used to deliver a drug, for example, a photo activator, to the blood. Yet another function that can be provided by the sheathing fluid is to cool the blood to compensate for heating by the light source 662. Any or all of these functions can be provided in various examples.

Blood treatment system 600 includes a separation channel 602 and, optionally a cooling heat exchanger 637 and/or a sheathing fluid reservoir 636. The separation channel 602 has inlet channels 608, 610 and 612 that lead to inlets 620, 621, and 622, respectively. The inlets 620 and 622 receive sheathing fluid from inlet channels 608 and 612, respectively. The inlet 621 receives blood from inlet channel 610. The inlets 620 and 622 can be filtered as described in more detail below with reference to FIG. 9. The separation channel 602 also has outlets 624, 625 and 626. The outlets 624 and 626 receive sheathing fluid and convey the same to outlet channels 614 and 618, respectively. Blood leaves the separation channel 602 through outlet 625 which conveys the blood to outlet channel 616. The outlets 624 and 626 can be filtered as described in more detail below with reference to FIG. 9. If filtering is provided on the inlets and/or outlets, the filters can have a pore size of about 60 nm, for example.

A patient (human or animal) 628 supplies blood to the system. A plurality of pumps 629, 630, 632, 634 can be automatically operated by a controller 640. Blood is pumped to separation channel 602 through a blood inlet channel 610. Whole blood can be supplied from patient 628; however, the system could also function with a reservoir supplying the blood. Blood withdrawal pump 630 removes blood from the separation channel 602 through blood outlet channel 616 and conveys it back to the patient 628. Also, a blood pump 629, though not essential, can be provided in line 610 to pump blood from the blood supply 628 to the separation channel 602.

The flow of sheathing fluid into separation channel 602, through sheath inlet channels 608 and 612 through inlets 620 and 622, is controlled by sheathing fluid injection pump 632, which can provide sheathing fluid in equal parts to channels 608 and 612. The flow of sheathing fluid out of separation channel 602, through outlets 624 and 626 and into outlet channels 614 and 618 is controlled by sheathing fluid withdrawal pump 634, which can draws equal amounts of sheathing fluid out of channels 614 and 618. Pump 634 can be a double pump such as a two-chamber pump or two peristaltic pumps with rotors on a common shaft. Alternatively two separate pumps (not shown) can be used on each of the lines 614 and 618 and feedback-controlled to balance the flow through the lines 614 and 618 while regulating the total flow of sheathing fluid from the separation channel 602. Pump 632 can also be a double pump such as a two-chamber pump or two peristaltic pumps with rotors on a common shaft (not shown). Pump 632 can be replaced by two separate pumps (not shown) on each of the lines 608 and 612 which are feedback-controlled to balance the flow through the lines 608 and 612 while regulating the total flow of extraction into the membraneless processor 602. The use of separate pumps can also provide the ability to convey different fluids, or the same or different fluids at different rates, to inlet channels 608 and 612. Thus, the sheathing fluid entering inlet channel 608 can be substantially similar to, or different from, the sheathing fluid entering inlet channel 612. The disclosed examples are not limited by the particular types of pumps or flow rates, and it should be appreciated that many variations are possible.

Pumps 629, 630, 632, and 634 (or other possible pump arrangements) can be used to control the flows of the sheathing fluids and blood fluid so as to withdraw only the sheathing fluids or the sheathing fluids plus a prescribed amount of blood fluid through outlets 624 and 626. Likewise, pumps 630, 632, and 634, and if present, pump 629, can be controlled to regulate the flows of the sheathing fluids and blood fluid to regulate the contact between the cell-containing blood layers and inlets 620 and 622.

In an example, the above described configuration of FIG. 6 can be used to perform dialysis as well as photopheresis using PCT/US06/18008 incorporated herein. System 600 can also include a sheathing fluid reservoir 636. Sheathing fluid reservoir 636 provides a supply of fresh sheathing fluid (e.g., such as replacement fluid used in hemofiltration or dialysate for blood treatment embodiments) to the flow loop.

In blood treatment examples, the sheathing fluid can be provided to separation channel 602 (from separator 604 and/or optional sheathing fluid reservoir 636) by sheathing fluid injection pump 632 occupies no more than ⅔ of the cross-section of separation channel 602, with blood from blood supply 628 in the middle ⅓. Such a flow configuration is illustrated in FIG. 1a. This configuration can be maintained by appropriately regulating the inflow of blood and sheathing fluid. As explained above, the plasma that is skimmed from the blood using separation channel 602 is returned to the sheath inlet channels 608 and 612 so that vital blood components are not lost. Because cell contact on the liquid-liquid contact area is far less traumatic, mechanically and chemically, a reduction in bio-incompatibilities and a reduced (or eliminated) need for anticoagulation is achieved. Additionally, because the primary transport surface in the system is intrinsically non-fouling and the surface of the filters is swept clean by the fluid shear rate, a major deterrent to long-term or continuous operation is removed, opening the possibility of a wearable system with the recognized benefits of prolonged, slow exchange.

It will be appreciated that long-term stability is necessary for satisfactory operation of the microfluidic devices described herein. For example, it is desirable to prevent inappropriate differences in sheath inlet and outlet channel flows, which, uncorrected, could result in unintended infusion of sheathing solution into the bloodstream. Accordingly, on-board electronics and photonics (not shown), which are common features of chip-based microfluidic devices, can be used to regulate system 600 (e.g., to introduce flow changes) with an electrically activated device (e.g., a piezoelectric valve) that is mounted on the same plate, or "chip," on which separation channel 602 is located.

An ultramicroscope or other device that is sensitive to the presence of dilute particles can be used to monitor the fluid exit stream in the sheathing fluid outlet channels 614 and 618 for the presence of cells in the sheathing fluid. The total volume of the sheathing fluid should be small to protect against flow imbalances that might cause blood losses or hypervolemia. For example, a control system can be provided which shuts down the system and initiates an alarm when cells are detected in the sheathing fluid outside the membraneless processor or when independent flow measuring sensors detect a flow imbalance between blood and net sheath flow beyond a threshold imbalance, which might obtain when a prescribed quantity of plasma is removed or when hypervolemia is being treated.

In examples, the photopheresis device 600 can have a cooling heat exchanger 637 to remove heat from the recirculating stream, thereby compensating for any heat conveyed to the blood stream by the light sources 662. The heat exchange may not be necessary, for example, if the light sources do not generate large amounts of heat, the heat exchanger can be eliminated. FIG. 7 shows another example of an extracorporeal photopheresis microfluidic device in which, instead of using capillaries of glass or some other transparent material, light can be conveyed by intercalating through the pores of filter fibers. Thus, a somewhat conventional dialyzer could be used to provide photopheresis. In FIG. 7, a standard dialyzer 700 is configured for use as an extracorporeal photopheresis device. As known in the prior art, a dialyzer of conventional construction has a cylindrical bundle of hollow filter fibers (or tubules) 710 enclosed within cylindrical shell 704 of the dialyzer. The filter fibers 710 constitute capillaries and serve as the microfluidic separation channels conveying blood between an inlet 702 and an outlet 712. The filter fibers 710 can be subject to irradiation by a therapeutic light source, as described in other examples herein, to achieve photopheresis with blood circulated into the dialyzer in the standard manner. Similar to the examples presented herein, the flow configuration is controlled such that the flow strain profile causes margination of the leukocytes within the filter fibers 710. The leukocytes can then be illuminated by one or more elongate therapeutic light sources 706. The elongate sources 706 can be integrated with a housing of the dialyzer 700 and/or arranged external to the dialyzer 700 around a periphery of a transparent wall of the housing. The interior of the dialyzer around filter fibers 710 can be filled with a conventional dialysate 708 which may or may not be circulated. The dialyzer-type device of FIG. 7 can be configured with filter fibers that are less densely packed than in a standard dialyzer such that light from an external therapeutic source can reach the innermost filter fibers. Although from an optical efficiency standpoint, the example of FIG. 7 may not be ideal, if a patient must undergo photopheresis and dialysis simultaneously, this can be a desirable configuration.

FIG. 8 illustrates a photopheresis module 844 with multiple separation channels 850 arranged in a stack. Light guides 852 are sandwiched between the separation channels 850 to distribute light from the therapeutic light sources 822 to the major faces of the separation channels 850. Inlet manifold 840 and outlet manifold 842 distribute blood and, if used, sheathing fluid, via respective channels (tubes) 832, 834, 836, and 838 to the separation channels 850. A light blocking (and reflecting) enclosure 860 can be provided.

Figure 9:
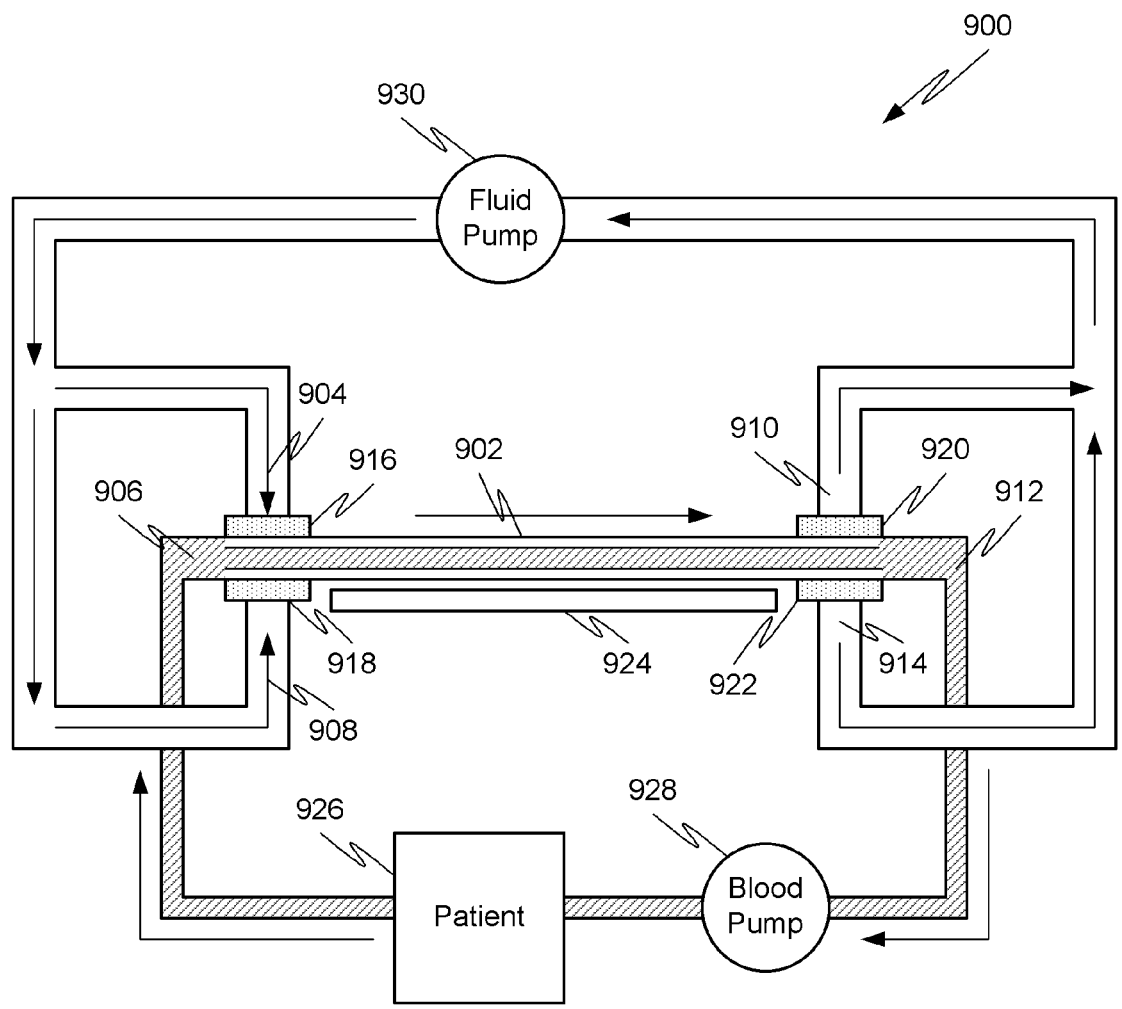
FIG. 9 shows an extracorporeal photopheresis microfluidic device with integrated membranes.

FIG. 9 illustrates an example of an extracorporeal photopheresis microfluidic device in which filters are employed in the separation channels to prevent blood cells from inadvertently exiting the channel with the sheath flow. As such, the embodiment of FIG. 9 is similar to that of FIGS. 3b and 6, but with the distinction that the microfluidic device 900 is provided with integrated membrane filters in the sheathing fluid flow paths, as discussed in PCT/US06/18008 incorporated herein.

The microfluidic device 900 includes three separate inlet channels 904, 906 and 908 and three corresponding outlet channels 910, 912 and 914. The flow of blood entering microfluidic separation channel 902 through inlet 906 is controlled such that stratification of the leukocytes is achieved, as discussed above. Sheathing fluid is pumped by pump 930 through inlets 904 and 908 in the direction of the blood flow and along the length of the channel illuminated by source 924. The sheathing fluid then exits at outlets 910 and 914 while the blood exits the microfluidic separation channel at outlet 912. Filter membranes 916, 918, 920, and 922 are respectively provided at each inlet and outlet for the sheathing fluid. As described in PCT/US06/18008 incorporated herein, the filter membranes provide a barrier to any cells that can migrate into the sheathing fluid flow path. Thus, even in the event of erratic leukocyte or erythrocyte flow behavior, the cells will be confined to the microfluidic separation channel 902 and thus be returned to the patient 926 through blood pump 928. Further, since the sheathing fluid is part of a recirculating system using fluid pump 930, any non-cellular blood components that migrate into the sheathing fluid flow and pass through the filters are not lost from the system but can be eventually returned to the blood during recirculation. As previously discussed, this device can be used to perform a dialysis-like treatment as well as photopheresis in a single operation. That is, the present configuration of the microfluidic photopheresis device can be similar to that described for microfluidic membrane-less exchange devices for blood dialysis with features such as described in PCT/US06/18008 incorporated herein.

Figure 10:
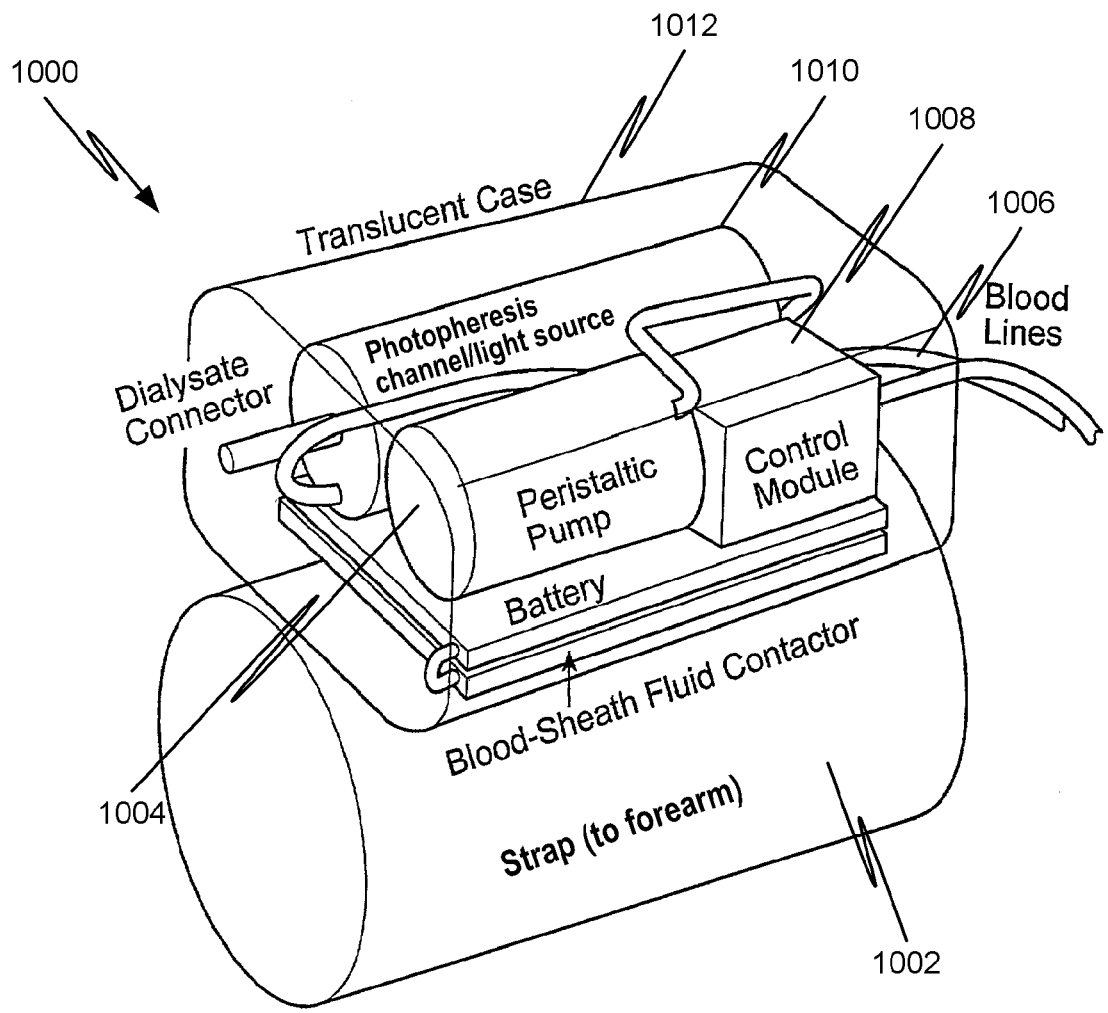
FIG. 10 is a schematic drawing of a wrist-size wearable photopheresis treatment system with a compact microfluidic separation channel or channels in a module small enough to be worn on a forearm.

FIG. 10 is a schematic illustration of a wrist-size wearable photopheresis treatment system 1000 with a compact microfluidic separation channel or channels 1010 in a module 1012 small enough to be worn on a forearm. A strap 1002 can be used to secure the system 1000 to the forearm of a patient. A peristaltic pump 1014 pumps blood through inlet blood line 1006 from a patient access, such as a button hole fistula or a central line. A control module 1008 controls the pump 1004, and a battery supplies power. The separation channel and therapeutic light source can be commonly housed in a light-shielded housing.

Therapeutic light sources, for example light sources 202, 202a, 404, 662, 706, 822, and 924 as identified here and elsewhere in the instant disclosure, can include convective cooling to minimize heating of blood in the separation channels. The therapeutic light sources can also include filters to block all but a desired one or more wavelengths that are most effective for treatment. Also, the separation channels and/or therapeutic light sources can be provided with additional air or liquid cooling to prevent radiant heating. For example, air or other fluid can be pumped around the light source to remove heat.

The materials for the microfluidic separation channels are limited only by the necessary material transparency at the illumination wavelength and biocompatibility with the fluid. Accordingly, a variety of materials capable of being fabricated into a microfluidic separation channel can be used, including, for example, glass and polymers. Illustrative examples of materials for the microfluidic separation channel include glass (e.g., borosilicate glass), polymers (e.g., polydimethylsiloxane (PDMS)), and semiconductor materials (e.g., silicon).

A working example of a suitably sized and shaped microfluidic separation channel can be fabricated as described in PCT/US06/18008 incorporated herein. In such an example, a separation channel can be fabricated using PDMS. To construct the microfluidic separation channels using PDMS, flat strips of copper foil, 100 μm thick, can be used as templates for the channels. The copper foil can be coated with a mold release agent. This copper foil can be placed in a Petri dish, after which an amount of PDMS precursor/curing agent mixture (10:1 ratio) sufficient to form a two centimeter-thick polymer layer after curing is poured thereon. After curing, the foil assembly can be released from the PDMS replica. The replica can be sandwiched between two partially cured flat pieces of PDMS and annealed to form a well-sealed channel. Finally, a slight vacuum can be applied during the annealing to remove air bubbles trapped between the microfluidic separation channel portion and the flat pieces. The device can be used after it is rinsed with ethanol and deionized water and dried with compressed nitrogen gas. A flat piece of PDMS can serve as a cover to seal the chip by adhesion. It will be understood that the particular fabrication process described above is for purposes of illustration only.

In another illustrative example of a fabrication process, microfluidic structures can be realized in PDMS (silicone) resin by replica-molding from master structures created in thick negative photo resist (SU-8) by optical lithography. Commercially available, standard grade mixtures of EPON SU-8 photo resist, SU-8-5 (52% solids), SU-8-25 (63% solids), SU-8 50 (69% solids) and SU-8 100 (73% solids), for example, can be spun onto silicon wafer substrates at a speed of rotation that depended on the film thickness needed, yielding films that are 10 to 300 μm thick. For example, SU-8 50 spun at 1100 rpm yields a 100 μm film. Prior to exposure, the spun layer can be baked on a precisely leveled hot plate at 95° C. for a time that is dictated by the film thickness (ranging from minutes to hours). These samples can be allowed to cool before further processing. Post-bake exposure, meanwhile, can be done using a direct laser writing system. The photolithographic setup can include an Ar-ion laser (wavelength=350 nm), focusing optics, and a computer controlled sample stage. Movement of the stage along all three axes (x, y, z) can be achieved by stepping motors or servo motor drives. Desired master patterns can be created by translating the samples underneath the focused laser beam to expose the outline, and then scanned across the interior so that the intended pattern is fully exposed. Dynamic focus correction of sample tilt with respect to the scanning laser beam can be done by on-the-fly adjustments of the distance between the focusing lens and the sample stage. For example, the exposure can be carried out at 95° C. for 15 min. Development can be carried out in a commercial SU-8 developer for a time based on film thickness (with the sample being lightly stirred during development). Alternately, once the SU-8 film is spun, pre-baked and cooled as described above, a mask aligner can be used together with standard chromium masks (or transparency masks depending on the resolution required) to pattern the SU-8. The patterned SU-8 films can then be post-baked, and developed in the manner outlined above.

Patterns created in SU-8 can be used as molding masters for replication in PDMS. PDMS can be prepared from a mixture of PDMS precursor and curing agent (Sylgard 184 kit, Dow Corning) in a 10:1 ratio by weight. Before curing, the mixture can be placed in vacuum to evacuate bubbles formed during mixing. The PDMS mixture can then be poured over the SU-8 master, which had been previously coated with a thin layer (~50 nm) of chromium to improve the release of the PDMS casting, after curing. Curing can be done at, for example, 70° C. for approximately twelve hours. Persons skilled in the applicable arts will appreciate that many other fabrication techniques can also be used to form the patterned molds and/or the microfluidic separation channel in accordance with the principles of the present disclosure.

While the discussion herein has been directed to extracorporeal photopheresis of leukocytes using blood flow margination, methods and systems in accordance with the scope of the present disclosure can be applied to other fluid systems as well. For example, the fluid need not be blood, nor does the isolated component have to be leukocytes. On the contrary, the scope of the present disclosure is intended to cover selective illumination of a component of a fluid flow by means of component segregation within the flow by margination. This fluid flow can be a blood flow, another biological fluid flow, or a general fluid flow. For example, fluorescent particles of various sizes in a biological fluid sample can be separated based on the margination effect to allow selective fluorescent excitation. Further, it would be apparent to those skilled in the art that the present extracorporeal photopheresis microfluidic device can be incorporated with other "lab on a chip" devices, such as a membrane-less microfluidic dialysis device, to form an integrated multi-function device.

It would be apparent to those skilled in the art that many advantages are provided in the various examples described herein. It should also be apparent that a device or system according to the present disclosure can be used to process the blood of a single individual for the purpose of treating any of a large number of disease states. For example, therapies according to the present disclosure can be used in the treatment of cutaneous T-cell lymphoma, cardiac, pulmonary and renal allograft rejection, autoimmune diseases, and ulcerative colitis. One skilled in the art will also appreciate that patients (or animals, in the case of veterinary use of aspects of the present disclosure) suffering from disorders, diseases and syndromes not listed herein can nonetheless be included in the patient pool intended for the device and system according to the present disclosure.

Additionally, the microfluidic devices and systems described above have a small need for supporting machinery and can be expected to be much smaller than conventional devices, to avoid high cell concentrations and channel wall contact, and to operate throughout at low rates of shear. Accordingly, they are especially compatible with cognate processes. In one example, a wearable (or at least portable) system according to the present disclosure can run between 20 and 24 hours per day at a flow rate of about 30 ml/min, for example. A patient could then have, for example, 4-5 hours each day without the device in place which could be used for personal hygiene (e.g., showers or baths), sports activities, or other activities not amenable to the small system being worn or used.

In another example, the microfluidic separation channel can be provided in a device that shunts blood from one blood vessel portion to another blood vessel portion using the natural blood pressure of the patient (person or animal) to drive the flow. For example, the separation channel can be configured as a shunt between an artery and a vein or as a connector between an upstream and a downstream part of a blood vessel. In such a device, a passive pressure-leveling device that absorbs and smoothes out pressure pulses can be provided, for example, a chamber with a compliant bladder or compliant walls.

In another example, the microfluidic separation channel or channels can be configured to separate blood to form a leukocyte-rich layer that flows in its own channel, is illuminated with light from the therapeutic light source, and then recombined with the remaining blood components. Because of the layering effect, a leukocyte-rich portion can be skimmed from the boundaries of the erythrocyte-rich layer and conveyed through a separate channel. Such a leukocyte-rich layer can include the plasma component or concentrate the leukocytes by skimming plasma into its own flow. Thus, for example, the sheathing fluid channel 613 of FIG. 6 can carry a leukocyte-rich fluid with plasma and the therapeutic light source 662 can be positioned to illuminate an irradiation flow channel continuous with the sheathing fluid channel 613. Such an irradiation channel can have the form of flat channels or cylindrical or any of the examples described herein and can be a single channel or multiple channels.

It is, therefore, apparent that there is provided, in accordance with the present disclosure, systems, methods, and devices for treatment of blood. Many alternatives, modifications, and variations are enabled by the present disclosure. Features of the disclosed examples can be combined, rearranged, omitted, etc., within the scope of the present disclosure to produce additional embodiments. Furthermore, certain features of the disclosed examples can sometimes be used to advantage without a corresponding use of other features. Persons skilled in the art will also appreciate that the present invention can be practiced by other than the described examples, which are presented for purposes of illustration and not to limit the invention as claimed. Accordingly, Applicants intend to embrace all such alternatives, modifications, equivalents, and variations that are within the spirit and scope of the present disclosure.

What is claimed is:

1. A method of performing photopheresis, comprising:
arranging leukocytes in blood from a living animal by creating a flow of the blood that generates a shear profile that causes leukocytes to be concentrated in a fraction of the flow;
illuminating the leukocytes in the fraction of the flow; and
returning the illuminated leukocytes to the living animal,
wherein the creating a flow of blood includes flowing the blood in a separation channel having a cross-section in a plane perpendicular to a direction of the flow, and the cross-section has an aspect ratio greater than 10 and a minimum dimension less than 200 μm,
wherein the illuminating includes using a therapeutic light source positioned so as to illuminate the concentrated leukocytes in the fraction of the flow in the separation channel without passing through a layer of erythrocytes in the separation channel.

2. The method of claim 1, wherein the flow is laminar.

3. The method of claim 1, wherein the illuminating includes generating light having a significant portion of its energy in the 200-400 nm wavelength range.

4. The method of claim 1, wherein the illuminating includes shining light on transparent walls of a channel containing the flow.

5. The method of claim 1, wherein the creating a flow of blood is such that erythrocytes in the flowing blood are at least partially shielded by the concentrated leukocytes from the illuminating.

6. The method of claim 1, wherein the flow of the blood is in a channel enclosed by a housing, and the therapeutic light source is positioned within said housing to illuminate the concentrated leukocytes in said channel.

7. The method of claim 1, wherein the illuminating includes directing light from the therapeutic light source onto one or more channels containing the flow of blood, the flowing in each channel being such that the concentrated leukocytes are between a wall of the channel and a layer of erythrocytes.

8. The method of claim 7, wherein the therapeutic light source and at least an illuminated portion of the one or more channels are enclosed in a common housing, and internal surfaces of the common housing are reflective.

9. The method of claim 7, wherein the illuminating includes using one or more optical elements in an illumination path between the therapeutic light source and the one or more channels so as to concentrate light from the source onto respective illuminated portions of the channels.

10. The method of claim 7, wherein the illuminating includes using one or more optical elements in an illumination path between the therapeutic light source and the one or more channels so as to uniformly illuminate respective illuminated portions of the channels.

11. The method of claim 1, wherein the illuminating includes directing light from one or more therapeutic light sources onto multiple channels, each channel containing a respective flow of blood.

12. The method of claim 11, wherein the multiple channels are arrayed with respect to each other such that light from the one or more therapeutic light sources illuminates concentrated leukocytes in each channel while erythrocytes in each channel are at least partially shielded from illumination.

13. The method of claim 1, wherein the creating a flow of the blood includes concentrating leukocytes in the fraction of the flow without removing other components from the blood.

14. A method of performing a photopheresis treatment on a patient, comprising:
flowing whole blood from the patient through a channel such that a shear profile causes leukocytes in the whole blood to segregate from other blood components flowing in the channel, the leukocytes being arranged in the flow between the other blood components and a wall of the channel in a cross-flow direction; and
at a same time as said flowing whole blood, illuminating with ultraviolet light through said wall of the channel the leukocytes in the flow while in the presence of the other blood components, the illuminating being sufficient to deliver a medically effective dose of ultraviolet light for said photopheresis treatment,
wherein the flow in the channel is laminar,
the channel has a minimum cross-flow dimension of less than 200 μm and a cross-section in a plane perpendicular to a direction of the flow, and
said cross-section has an aspect ratio greater than 10.

15. The method of claim 14, wherein said channel is in a portable treatment module worn by the patient.

16. The method of claim 14, further comprising conveying the illuminated leukocytes and the other blood components to the patient via a blood line directly connecting an outlet of the channel to an access of the patient.

17. The method of claim 14, further comprising, at a same time as the flowing whole blood, pumping sheathing fluid into the channel through a sheathing fluid inlet so as to flow in a same direction as the blood flow and to be between the leukocytes and the wall of the channel in the cross-flow direction.

18. The method of claim 17, further comprising, withdrawing the sheathing fluid from the channel through a sheathing fluid outlet having a filter member, the filter member being constructed to prevent leukocytes and erythrocytes from leaving the channel through said sheathing fluid outlet.

* * * * *